(12) United States Patent
Levy et al.

(10) Patent No.: US 7,922,851 B2
(45) Date of Patent: Apr. 12, 2011

(54) METHOD OF MANUFACTURING CLOSURE TABS FOR ABSORBENT ARTICLES

(75) Inventors: Ruth L. Levy, Collegeville, PA (US); Carol L. Erdman, West Chester, PA (US)

(73) Assignee: First Quality Retail Services, LLC, Great Neck, NY (US)

( * ) Notice: Subject to any disclaimer, the term of this patent is extended or adjusted under 35 U.S.C. 154(b) by 88 days.

(21) Appl. No.: 12/080,485

(22) Filed: Apr. 3, 2008

(65) Prior Publication Data

US 2009/0211691 A1    Aug. 27, 2009

Related U.S. Application Data

(62) Division of application No. 10/875,389, filed on Jun. 24, 2004, now Pat. No. 7,373,698.

(51) Int. Cl.
*B29C 59/00* (2006.01)
(52) U.S. Cl. .................. 156/209; 156/220; 156/222
(58) Field of Classification Search ............ 428/99, 428/100
See application file for complete search history.

(56) References Cited

U.S. PATENT DOCUMENTS

| | | | | | |
|---|---|---|---|---|---|
| 1,739,322 | A | * | 12/1929 | Moore | 428/85 |
| 2,331,054 | A | * | 10/1943 | Shively | 156/209 |
| 3,256,131 | A | * | 6/1966 | Koch et al. | 428/160 |
| 5,985,407 | A | * | 11/1999 | Murasaki | 428/100 |
| 6,332,250 | B1 | * | 12/2001 | Igaue et al. | 24/450 |
| 6,719,742 | B1 | * | 4/2004 | McCormack et al. | 604/385.01 |

* cited by examiner

*Primary Examiner* — John L. Goff
*Assistant Examiner* — Barbara J. Musser
(74) *Attorney, Agent, or Firm* — Amster, Rothstein & Ebenstein LLP (57) ABSTRACT

A closure tab is provided and includes a first substrate. A second substrate is adhesively attached to the first substrate. The second substrate has mechanical closure material formed thereon. A compression bond pattern is applied to the first substrate and the second substrate. The compression bond pattern includes at least one outwardly extending protrusion. The compression bond pattern may include, for example, circular bond points, stripes, or a decorative element. A method is also provided wherein the second substrate is compressed onto the first substrate by a patterned roller. The second substrate may be compressed onto the first substrate by a plurality of pins spaced in alternating offset rows.

8 Claims, 8 Drawing Sheets

METHOD OF MANUFACTURING CLOSURE TABS FOR ABSORBENT ARTICLES

This application is a divisional of U.S. patent application Ser. No. 10/875,389, filed Jun. 24, 2004 now U.S. Pat. No. 7,373,698.

BACKGROUND

1. Technical Field

The present disclosure generally relates to closure tabs for use on absorbent articles, and more particularly, to mechanical closure systems having greater integrity by the application of compression bonding.

2. Background of the Related Art

Absorbent articles such as, for example, disposable diapers, adult incontinent pads, sanitary napkins, pantiliners, incontinent garments, etc. are generally worn, in cooperation with garments and disposed against a body surface, etc., by infants or adult incontinent individuals. The absorbent article is employed to collect, absorb, etc. body fluid discharge, such as, for example, blood, menses, urine, aqueous body fluids, mucus, cellular debris, etc. For example, the absorbent article may be disposed between the legs of an individual adjacent a crotch area. The absorbent article is positioned with a garment and drawn into engagement with a body surface of the crotch area to collect fluid discharge.

As is known, absorbent articles typically include a fluid permeable coverstock for engaging the body surface, a fluid impermeable back sheet and an absorbent core supported therebetween. The backsheet serves as a moisture barrier to prevent fluid leakage to the garment. The absorbent core usually includes a liquid retention material that faces the body surface. The absorbent core can include loosely formed cellulosic fibers, such as wood pulp, for acquiring and storing fluid discharge.

Fastening of the absorbent articles with an individual requires the use of closure tabs or other closure systems employing fastening members. For example, in typical diaper-type garments, the garment is affixed to a wearer by attaching one or more closure tabs that extend across the wearer's hips to hold the back and front halves of the garment to one another. These closure systems typically include a fastening member or "tab material," and mechanical closure material (such as hook and loop material) attached to the tab material. This composite of tab material and the mechanical closure material is fixed or secured to the absorbent article. Generally, such securing to the absorbent article is accomplished by adhesive, ultrasonic bonding, stitching and the like.

The securing of the mechanical closure material to the fastening members of absorbent articles, however, may suffer from occasional separation and dislodging. These separations cause the closure system to fail, thereby preventing attachment of the absorbent article to an individual and rendering such absorbent article ineffective. Failure can also occur, for example, because wearers typically move their bodies while the fasteners are attached, sometimes causing the closure tabs to become loose, uncomfortable or even unfastened. Yet another factor complicating the task of fastener tab design is the fact that the caregivers applying the tabs do so in a variety of ways that may or may not be suitable to properly affix tabs of the particular design being applied. Moreover, these drawbacks can disadvantageously result in wasted product and unpleasant product experience for the consumer.

Despite these and other efforts by absorbent garment manufacturers and others to provide suitable closure tabs for absorbent garments, there is still a need to provide a more comfortable, better fitting, and easily applied tab. These are just a few of the disadvantages of the prior art that the preferred embodiments seek to address. It would therefore be desirable to overcome the disadvantages and drawbacks of the prior art by providing a closure tab that contains hook and loop material that is securely and permanently attached thereto. It would also be desirable if the secure attachment of the hook and loop material to the tab material is easily and more efficiently manufactured.

SUMMARY

Accordingly, a closure tab and manufacturing process is disclosed that includes a closure tab with hook and loop material that is securely and permanently attached to fastening and attachment members. The method of attaching the hook and loop material and its constituent parts are easily. and efficiently manufactured. Other objects and. advantages of the present disclosure are set forth in part herein and in part will be obvious therefrom, or may be learned by practice of the present disclosure that is realized and attained by the instrumentalities and combinations pointed out in the appended claims for the devices and methods of the present disclosure consisting of its constituent parts, constructions, arrangements, combinations, steps and improvements herein shown and described.

The closure tabs of the present disclosure may include fastening and/or attachment members that include hook and loop attachment with greater integrity and security by way of mechanical application of compression bonding. The advantage of this construction provides for a manufacturing process and travel path that includes less manufacturing errors and down time due to the higher incidence of secure and permanent hook and loop material attachment.

In one particular embodiment, a closure tab is provided, in accordance with the principles of the present disclosure. The closure tab includes a first substrate and a second substrate. The second substrate is adhesively attached to the first substrate. The second substrate has mechanical closure material formed thereon. A compression bond pattern is applied to the first substrate and the second substrate. The compression bond pattern includes at least one outwardly extending protrusion. The compression bond pattern may include, for example, circular bond points, stripes, or a decorative element. More specifically, the second substrate is compressed onto the first substrate by a patterned roller. The second substrate may be compressed onto the first substrate by a plurality of pins. The second substrate may be a laminate of two or more materials.

The plurality of pins may be spaced in alternating offset rows. The plurality of pins can have a height of approximately 0.020" to 0.060" inches. The plurality of pins are configured so not to crush/deform a majority of closure members on the mechanical closure material. Further, the pins are configured so not to perforate the first or second substrates. The second substrate is attached to the first substrate by a plurality of compression bond points. The compressions bond points act to reduce longitudinal shear between the first and second substrates. More specifically, the compression bond points deform a portion of the first substrate and the second substrate.

In another embodiment, a method for making the closure tab is provided. The method includes the steps of providing a first substrate, similar to that described; adhesively adhering a second substrate, similar to that described, to the first substrate; and compressing the first substrate to the second substrate with a patterned roller. The step of compressing the first substrate to the second substrate may include a patterned roller having a plurality of pins. The plurality of pins are configured not to crush a majority mechanical closure members formed on the second substrate. In addition, the plurality of pins are configured not to perforate the first and second substrate. The compressing step may further include compressing the second substrate to a degree that deforms a base material of the second substrate. Preferably, at least ten percent (although other percentages are contemplated) of a thickness/width of the base material of the second substrate is deformed into an adhesive and the first substrate to further secure the second substrate to the first substrate. Desirably, the deformation of the second substrate does not perforate the first substrate.

BRIEF DESCRIPTION OF THE DRAWINGS

The objects and features of the present disclosure are set forth with particularity in the appended claims. The present disclosure, as to its organization and manner of operation, together with further objectives and advantages may be understood by reference to the following description, taken in connection with the accompanying drawings, in which:

DETAILED DESCRIPTION OF EXEMPLARY EMBODIMENTS

The exemplary embodiments of the closure tab and methods of manufacture disclosed are discussed in terms of an absorbent article including a closure tab with hook and loop material that is securely and permanently attached to fastening and attachment members. The presently disclosed closure tab includes include hook and loop attachment with greater integrity and security by way of mechanical application of compression bonding. It is contemplated that the closure tab may be employed with absorbent articles such as disposable diapers, adult incontinent pads, feminine pads, sanitary napkins, incontinent garments, or other articles intended to avoid leakage, overflow, etc., of fluid discharge, such as, for example, blood, menses, urine, aqueous body fluids, mucus, cellular debris, etc.

In the case of diapers and most adult incontinent products, the garment often is provided fully formed with factory-made side seams and the garment is donned by pulling it up the wearer's legs. In the case of diapers, wherein, for example, a baby lies on his or her back, a caregiver usually places the diaper between the baby's legs, pulls the front end of the diaper up between the legs and then attaches one or more closure tabs to the rear end of the diaper, thereby forming a pant-like structure.

In the discussion that follows, the term "body facing surface" refers to a portion of a structure that is oriented towards a body surface, and the "garment facing surface" refers to a portion of the structure that is oriented towards a garment and is typically opposing the body facing surface and may be referred to as such. As used herein, the term "body surface" refers to a portion of an individual's body that the absorbent article is disposed with for collecting, absorbing, etc. fluid discharge from the individual.

The following discussion includes a description of an absorbent article including a closure tab, followed by a description of a method of manufacture in accordance with the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1-7, there is illustrated a closure tab(s) 33, constructed in accordance with the principles of the present disclosure. Closure tabs 33 may be used to fasten absorbent articles, such as, for example diaper 10. Diaper 10 includes a backsheet 12 bonded to a topsheet 14 and an absorbent core 16 disposed therebetween. Diaper 10 extends from a rear end 18, configured for engagement with a rear portion of a subject, to a front end 20, configured for engagement with a front portion of a subject, along a longitudinal axis x defined by diaper 10. Each of two lateral extensions 34 is made from partially elastic material and is adhesively bonded to respective opposite sides 24, 26 of rear end 18. Lateral extension 34 is extensible in a direction along transverse axis y relative to longitudinal axis x. Each of closure tabs 33 is attached distally to respective lateral extensions 34 by adhesive bonding. It is contemplated herein that lateral extensions 34 and closure tabs 33 may be formed with materials that are elastic, non-elastic or a combination thereof.

Figure 2:
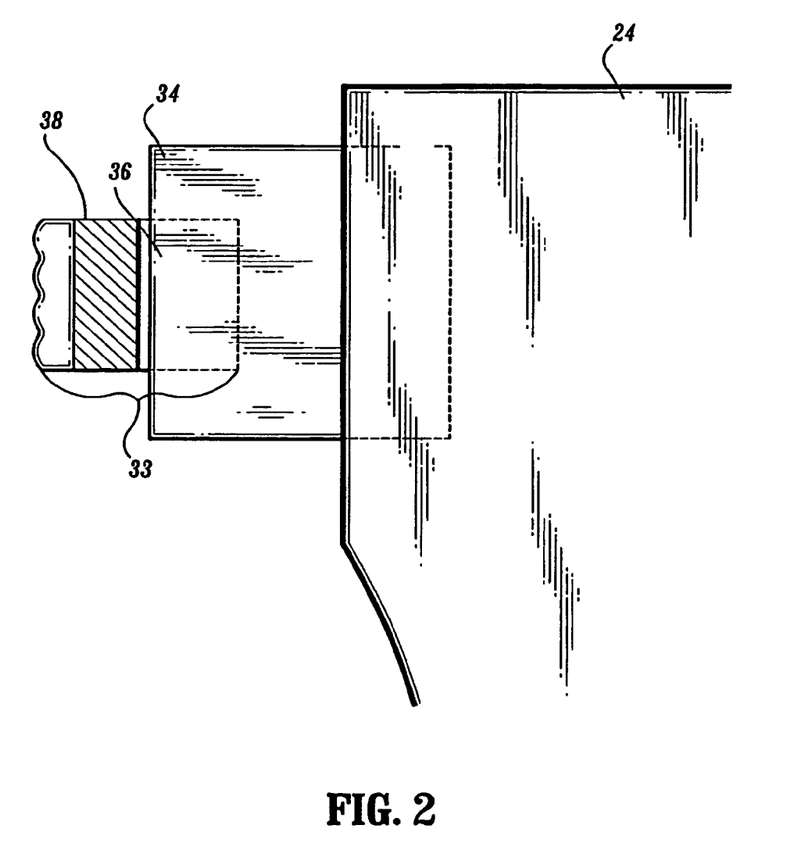
FIG. 2 is an enlarged cutaway view of the absorbent article illustrating a closure tab shown in FIG. 1.
Figure 3:
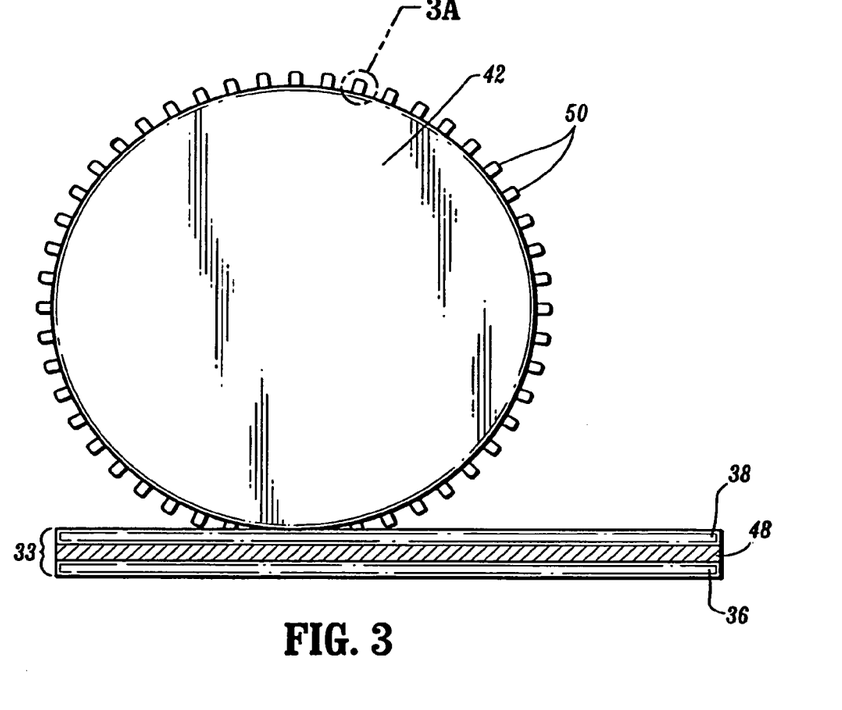
FIG. 3 is a side view of a manufacturing process including a patterned roller used in making the closure tab shown in FIG. 1.
Figure 3A:
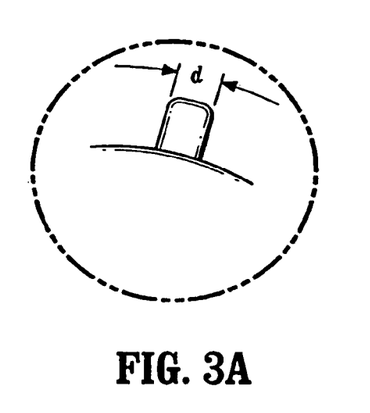
FIG. 3A is an enlarged view of the indicated area of detail in FIG. 3.

Closure tab 33 comprises a first substrate, such as, for example, tab material 36 and a second substrate, such as, for example, a mechanical closure material employing hook or loop. Mechanical closure material includes a substrate or base 39 having formed thereon a plurality of hooks, loops or the like. that mate with a partner material on diaper 10. In the illustrative embodiment, mechanical closure material or hook member includes hook stems or hooks 40 formed thereon and is herein referred to as hook material or hook member 38. Hook member 38 is adhesively attached to tab material 36. It is contemplated that either of hook member 38 or tab material 36 may comprise a laminate of two or more materials.

Figure 1:
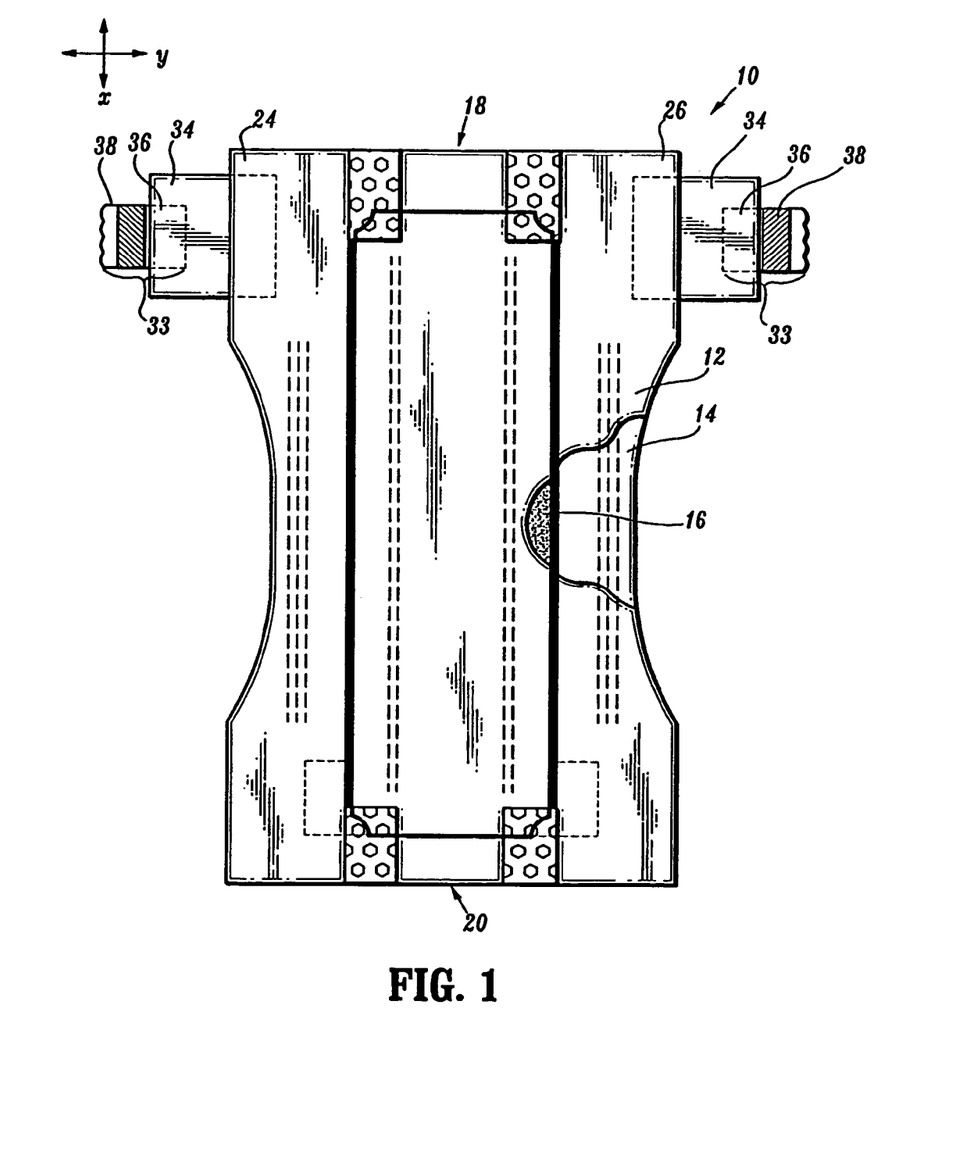
FIG. 1 is a plan view of an absorbent article including closure tabs in accordance with the principles of the present disclosure.

Hook member 38 may comprise any hook-and-loop type fastener, adhesive fastener, or other type of fastener that is capable of holding diaper 10 on a wearer. Suitable hook-and-loop fasteners are readily available from 3M Corp. (St. Paul, Minn.), Aplix, Inc. (Charlotte, N.C.), and Velcro USA, Inc. (Manchester, N.H.). Hook member 38 operates by engaging with or adhering to a corresponding surface or object (not shown) located on the opposite end of the diaper 10, for example, front end 20.

The present disclosure provides an improved closure tab 33 wherein a compression bond pattern 44 is applied to hook member 38 and tab material 36. This compression bond provides an improvement in the adhesion between hook member 38 and tab material 36. In the illustrative embodiments, a patterned roller 42 is used to compress hook member 38 onto tab material 36. Alternatively, a patterned stamp (not shown) or other means may be used to apply compression bond pattern 44.

Figure 4:
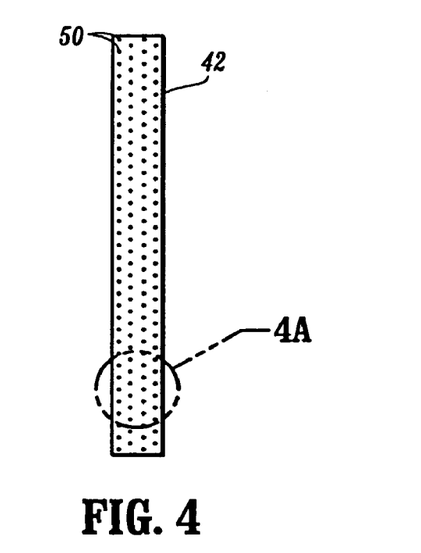
FIG. 4 is a front view of the patterned roller shown in FIG. 3.
Figure 4A:
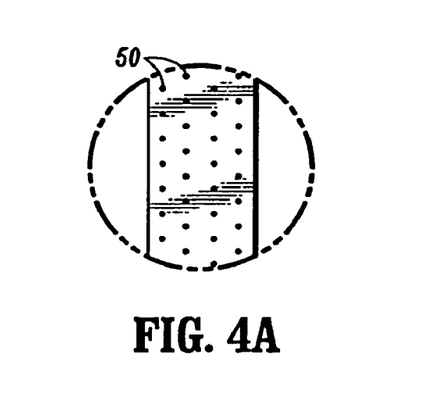
FIG. 4A is an enlarged view of the indicated area of detail in FIG. 4.
Figure 5A:
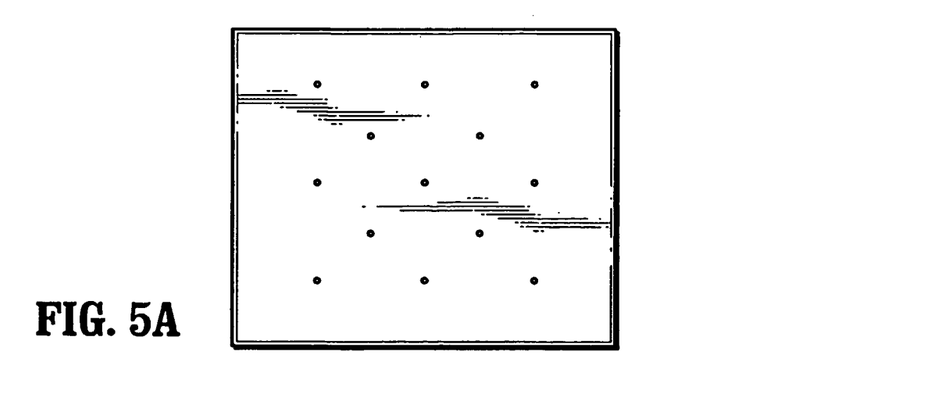
FIG. 5A is a front view of a compression bond pattern applied to the closure tab shown in FIG. 1.
Figure 5B:
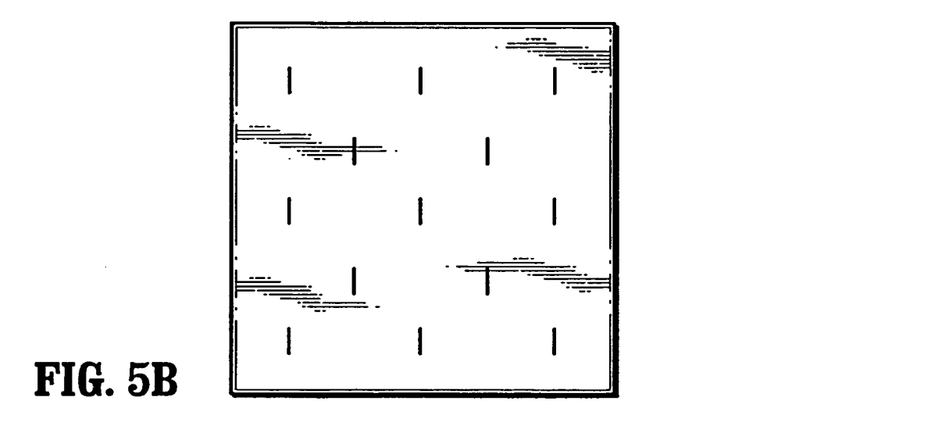
FIG. 5B is a front view of an alternative compression bond pattern applied to the closure tab shown in FIG. 1.
Figure 5C:
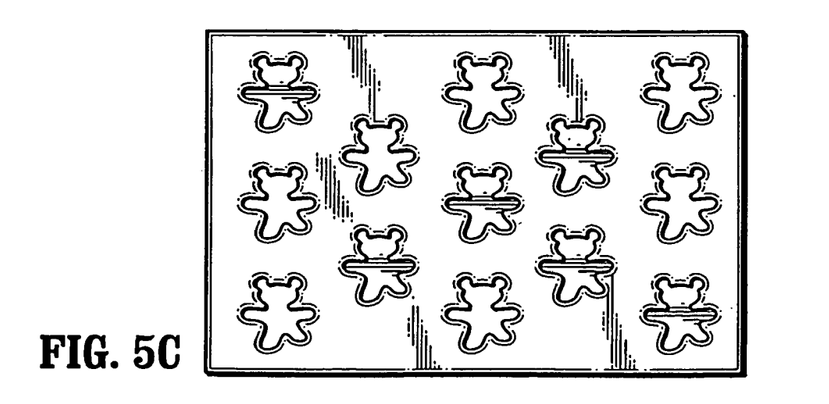
FIG. 5C is a front view of another alternative compression bond pattern applied to the closure tab shown in FIG. 1.
Figure 5D:
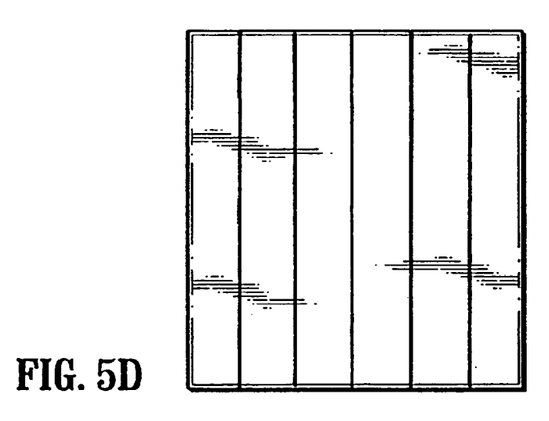
FIG. 5D is a front view of another alternative compression bond pattern applied to the closure tab shown in FIG. 1.

Patterned roller 42 has a plurality of outwardly extending protrusions 50 on the roller's external circumference. In the illustrative embodiment, the roller comprises an anvil 42 having a plurality of pins 50 formed on a circumference thereof. Pins 50 have a height of approximately 0.020 to 0.060 inches, and a diameter d. Alternatively, the height of a respective pin 50 may be a percentage of the thickness T of hook base 39. Pins 50 are spaced on the anvil's circumference in a plurality of alternating offset rows. The number of rows may be based on, for example, the width of hook member 38, or the diameter(s) of pins 50 and/or hooks 40. While the illustrative embodiment includes five (5) pin rows, there could be more rows if a wider hook member 38 was used. Consequently, as the pinned anvil 42 compresses hook member 38 onto tab material 36, pins 50 apply thereto a pattern 44 of deformations, bond zones or bond points 46.

Figure 6:
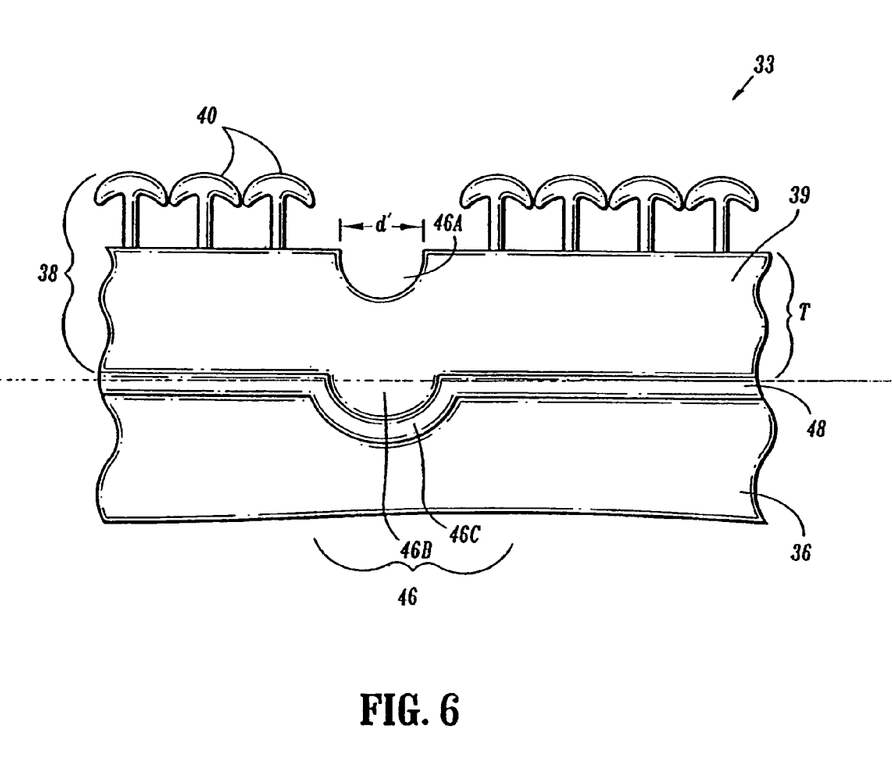
FIG. 6 is a enlarged cutaway side view of the closure tab shown in FIG. 1.

More specifically, as pinned anvil 42 rotates over and exerts pressure on hook material 38 and tab material 36, these materials 36, 38 come into contact with pins 50 on the anvil's circumference. Consequently, each pin 50 forms a deformation or a set of deformations 46a, 46b, and 46c as shown in FIG. 6. In particular, pins 50 deform hook material 38 into adhesive 48 and tab material 36 to further secure hook material 38 to tab material 36. This will be described in more detail later with regard to a method for manufacturing closure tab 33.

Instead of pins 50, patterned roller 42 may comprise protrusions having other shapes so to apply various compression bond patterns 44 to hook member 38 and tab material 36. For example, a plurality of elongated protrusions would result in a bond pattern 44 of stripes or the like (not shown). Other suitable bonding patterns include circles, squares, triangles, diamonds, waves, dashes, etc. Alternatively, compression bond pattern 44 may comprise a decorative pattern or element, such as a teddy bear, logo, or the like (FIGS. 5A-5D).

Applicants recognize that hook member 38 loses function in proportion to the number of individual hook stems 40 that may be crushed or deformed by pins 50 as roller 42 compresses hook member 38 to tab material 36. Advantageously, pattern roller 42 is designed to avoid crushing or deforming hooks 40, while providing enhanced integration of an adhesive 48 with hook member 38 and tab material 36. For example, compression pattern 44 of circular bond points 46 may be in offset rows. With this pattern 44, pins 50 are spaced far enough apart from each other so not to crush a majority of the plurality of hooks 40. In addition, each bond point 46 has a diameter d' sufficiently small not to crush hooks 40, yet large enough not to push through or perforate hook member 38 or tab material 36 (FIG. 6). Accordingly, compression bond pattern 44 may be suitably applied to hook members 38 having a variety of hook densities and configurations.

In this regard, FIG. 6 is an enlarged cutaway side view of closure tab 33. Hook member 38 is attached to tab material 36 by a plurality of compression bond points 46 (only one bond point 46 is shown). To form compression bond point 46, each pin 50 deforms a portion of hook member 38 and tab material 36. These deformations include deformations 46a, 46b, and 46c. Preferably, at least ten percent (although other percentages are contemplated) of the thickness of hook substrate 39 is deformed into adhesive 48 and tab material 36, to further secure hook member 38 and tab material 36. Consequently, compression bond points 46 reduce longitudinal shear between hook member 38 and tab material 36. In this regard, deformations 46b and 46c interfere with each other and thus contribute to reducing shear.

A method of manufacturing a closure tab 33, similar to that described, in accordance with the principles of the present disclosure is provided. The process can best be understood by reference to an illustrative embodiment shown in FIG. 7. A generally continuous length of hook material 38 is provided from supply roll 60. Adhesive 48 is applied to hook material 38 by applicator 62. Tab material 36 is provided from supply roll 64 and has a width W'. Hook material 38 is adhered to tab material 36 as a result of adhesive 48 applied to hook material 38 by applicator 62. Nip rollers 66 facilitate adhesive contact between hook material 38 and tab material 36. The adhering of hook material 38 to tab material 36 forms a composite 70.

Figure 7:
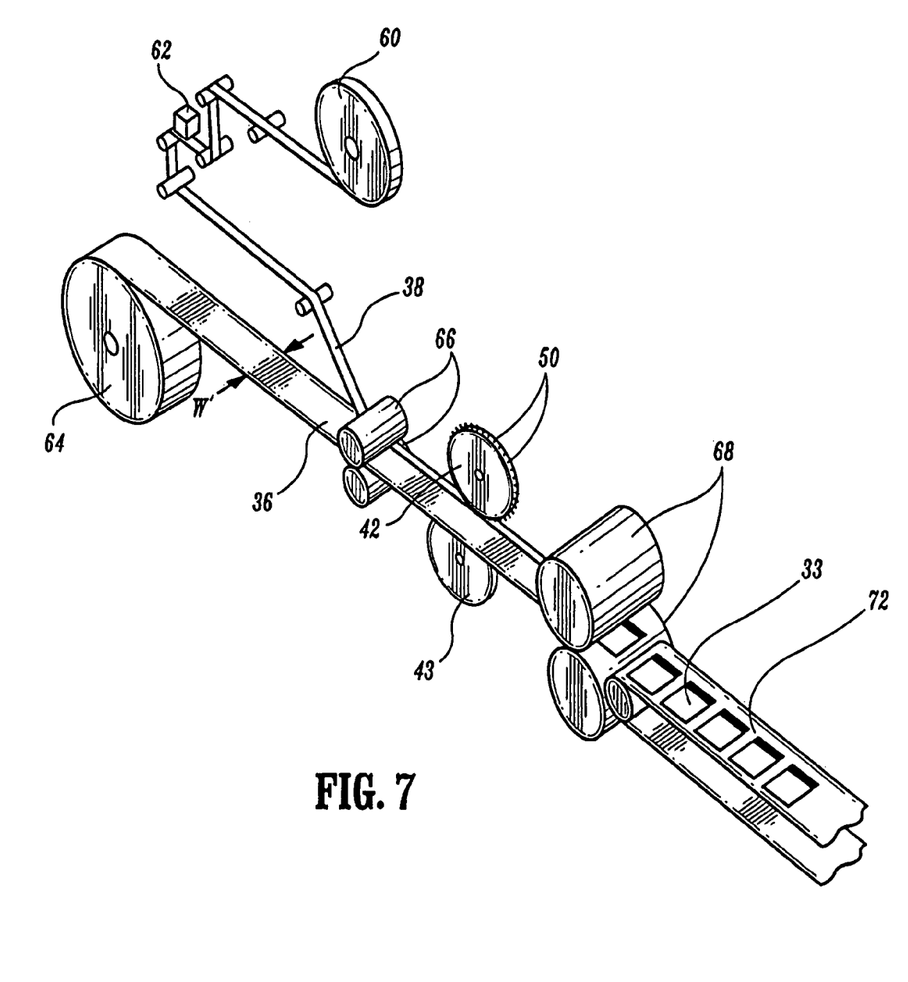
FIG. 7 is a perspective view of a manufacturing process for making the closure tab shown in FIG. 1.

Other means of adhering hook material 38 to tab material 36 are contemplated. For example, in addition to adhesive attachment, it is possible to thermally bond (including ultrasonic bonding), chemically bond, or sew hook material 38 to tab material 36. Alternatively, hook material 38 can be purchased with adhesive 48 already applied. It is further envisioned that adhesive 48 may be applied to tab material 36 (instead of hook material 38) by applicator 62. Applicator 62 may comprise, for example, a slotcoater, spray applicator, bead applicator, curtain applicator, or printer.

Composite 70 of hook material 38 and tab material 36 then travels towards pinned anvil 42 and smooth roller 43 opposed thereto. As pinned anvil 42 exerts pressure on/compresses composite 70, pins 50 engage composite 70 and apply a pattern 44 of bond points 46 thereto, similar to that described. More specifically, pins 50 deform base portion 39 of hook material 38 into adhesive 48 and tab material 36 to further secure hook material 38 to tab material 36. Each pin 50 creates a set of deformations 46a, 46b, and 46c. Preferably, at least ten percent (although other percentages are contemplated) of a thickness/width of hook base material or substrate 39 is deformed into adhesive 48 and tab material 36. The deformation does not perforate hook material 38 and tab material 36.

Composite 70 is then cut by cutter 68 to form individual closure tabs 33. Closure tabs 33 are then conveyed on conveyer 72 to a location for application to an absorbent article.

Cutter 68 may comprise rotary cutters, air knives, thermal knives, pinch cutters, ultrasonic cutters, lasers, and the like. Conveyor 72 may comprise a conveying belt, vacuum drum, transfer layers, gripper fingers, and the like. It is envisioned that the process of applying bond pattern 44 to composite 70 may be performed separate from the process of applying adhesive 48 to hook material 38 or tab material 36, and separate from the process of cutting closure tabs 33.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method of forming a closure tab comprising:
adhesively attaching a first substrate to a second substrate using adhesive, the second substrate having a mechanical closure formed thereon; and
applying a compression bond pattern to the first substrate and the second substrate without a thermal bond, wherein the compression bond pattern defines deformations comprising a portion of the second substrate deformed into each of the adhesive and a portion of the first substrate.

2. The method of claim 1, wherein the compression bond pattern includes at least one deformation.

3. The method of claim 1, wherein the compression bond pattern includes at least one stripe.

4. The method of claim 1, wherein the compression bond pattern includes a decorative element.

5. The method of claim 1, wherein a plurality of compression bonds of the compression bond pattern are spaced in alternating offset rows.

6. The method of claim 1, wherein a majority of closure members on the mechanical closure material are not deformed.

7. The method of claim 1, wherein the first or second substrates are not perforated.

8. The method of claim 1, wherein the deformations extend at least ten percent into a thickness of the first substrate.

* * * * *